(12) United States Patent
Davydov et al.

(10) Patent No.: US 11,286,217 B2
(45) Date of Patent: Mar. 29, 2022

(54) PROCESS AND APPARATUS FOR REACTING FEED WITH FLUIDIZED CATALYST AND CONFINED QUENCH

(71) Applicant: UOP LLC, Des Plaines, IL (US)

(72) Inventors: Lev Davydov, Northbrook, IL (US); Richard A. Johnson, II, Algonquin, IL (US)

(73) Assignee: UOP LLC, Des Plaines, IL (US)

( * ) Notice: Subject to any disclaimer, the term of this patent is extended or adjusted under 35 U.S.C. 154(b) by 113 days.

(21) Appl. No.: 16/942,113

(22) Filed: Jul. 29, 2020

(65) Prior Publication Data

US 2022/0033326 A1    Feb. 3, 2022

(51) Int. Cl.
| | | |
|---|---|---|
| C07C 5/00 | (2006.01) | |
| C07C 5/333 | (2006.01) | |
| B01J 8/18 | (2006.01) | |
| B01J 8/26 | (2006.01) | |
| B01J 8/00 | (2006.01) | |

(52) U.S. Cl.
CPC .............. *C07C 5/333* (2013.01); *B01J 8/0055* (2013.01); *B01J 8/1827* (2013.01); *B01J 8/26* (2013.01); *B01J 2208/00761* (2013.01); *B01J 2208/00849* (2013.01)

(58) Field of Classification Search
CPC ..... C07C 5/3332; C07C 11/08; C07C 5/3337; C07C 11/06; C07C 11/09; C07C 11/167; C07C 2521/04; C07C 2521/08; C07C 2521/12; C07C 2523/08; C07C 2523/42; C07C 2523/62; C07C 2523/14; C07C 2523/26; C07C 5/333; B01J 38/02; B01J 38/12; B01J 8/0025; B01J 8/0055; B01J 8/1818; B01J 8/1827; B01J 21/04; B01J 21/12; B01J 23/26; B01J 23/62; B01J 7/00
See application file for complete search history.

(56) References Cited

U.S. PATENT DOCUMENTS

| | | | |
|---|---|---|---|
| 6,558,531 B2 | 5/2003 | Steffens | |
| 6,753,502 B2 | 6/2004 | Correia | |
| 9,266,103 B1 | 2/2016 | Davydov | |
| 9,597,652 B1 | 3/2017 | Pretz | |
| 9,889,418 B2 | 2/2018 | Pretz | |
| 10,227,271 B2 * | 3/2019 | Pretz | ........................ B01J 8/087 |

\* cited by examiner

*Primary Examiner* — Sharon Pregler
(74) *Attorney, Agent, or Firm* — Paschall & Associates, LLC; James C. Paschall

(57) ABSTRACT

A dehydrogenation process and apparatus contact a paraffinic stream with dehydrogenation catalyst to product olefinic product gases. The olefinic product gases are separated from spent dehydrogenation catalyst and contained in a confined space that has a smaller volume than the reactor particularly at the same elevation. The containment of the olefinic product gases facilitates quenching the olefinic product gases to terminate reaction and improve selectivity to propylene.

20 Claims, 1 Drawing Sheet

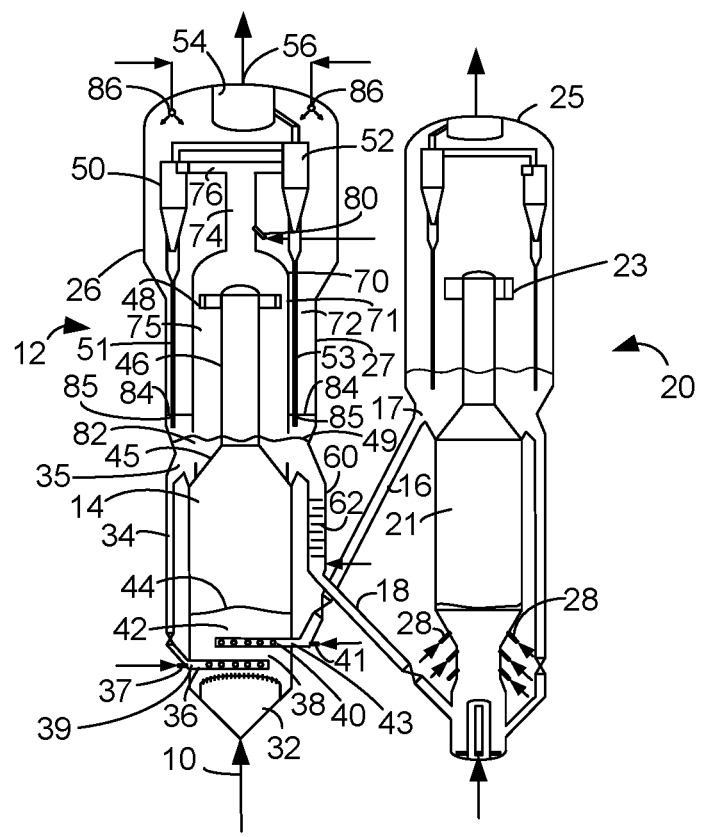

PROCESS AND APPARATUS FOR REACTING FEED WITH FLUIDIZED CATALYST AND CONFINED QUENCH

FIELD

The field is the reaction of feed with fluid catalyst. The field may particularly relate to reacting a paraffin feed with a fluid dehydrogenation catalyst.

BACKGROUND

Light olefin production is vital to the production of sufficient plastics to meet worldwide demand. Paraffin dehydrogenation (PDH) is a process in which light paraffins such as ethane and propane can be dehydrogenated to make ethylene and propylene, respectively. Dehydrogenation is an endothermic reaction which requires external heat to drive the reaction to completion.

Dehydrogenation catalyst may incorporate a dehydrogenation metal with a molecular sieve or an amorphous material. The catalyst must be sufficiently robust and appropriately sized to be able to resist the attrition expected in a fluidized system.

In PDH reactions with fluidized catalyst, coke can deposit on the catalyst while catalyzing the reaction. The catalyst may be regenerated in a catalyst regenerator by combusting coke from the catalyst in the presence of oxygen. The hot regenerated catalyst may then be transferred back to the reactor to catalyze the reaction. If insufficient heat is provided to drive the endothermic reaction, olefin production can suffer.

The catalytic reactions are more selective to the desired products such as propylene than the thermal cracking reactions. Care must be taken to maximize catalytic reactions over thermal cracking reactions to improve selectivity to propylene.

There is a need, therefore, for improved methods of contacting feed with catalyst in a fluidized catalytic reaction process.

BRIEF SUMMARY

A dehydrogenation process and apparatus are used to contact a paraffinic stream with dehydrogenation catalyst to product olefinic product gases. The olefinic product gases are separated from spent dehydrogenation catalyst and contained in a confined space that has a smaller volume than the reactor particularly at the same elevation. The containment of the olefinic product gases facilitates quenching the olefinic product gases to terminate reaction and improve selectivity to propylene.

BRIEF DESCRIPTION OF THE DRAWINGS

The FIGURE is a schematic drawing of a process and apparatus of the present disclosure.

DEFINITIONS

The term "communication" means that fluid flow is operatively permitted between enumerated components, which may be characterized as "fluid communication".

The term "downstream communication" means that at least a portion of fluid flowing to the subject in downstream communication may operatively flow from the object with which it fluidly communicates.

The term "upstream communication" means that at least a portion of the fluid flowing from the subject in upstream communication may operatively flow to the object with which it fluidly communicates.

The term "direct communication" means that fluid flow from the upstream component enters the downstream component without passing through any other intervening vessel.

The term "indirect communication" means that fluid flow from the upstream component enters the downstream component after passing through an intervening vessel.

The term "bypass" means that the object is out of downstream communication with a bypassing subject at least to the extent of bypassing.

As used herein, the term "predominant" or "predominate" means greater than 50%, suitably greater than 75% and preferably greater than 90%.

DETAILED DESCRIPTION

We have discovered a dehydrogenation process and apparatus for terminating the dehydrogenation and other reactions that are not selective to producing propylene or other desired olefin. Dehydrogenation catalyst and olefinic product gases are separated from each other in a primary catalyst separator. More than 90 wt % of dehydrogenation catalyst can be separated by a primary catalyst separator. The separated olefinic product gases are confined in a containment space to facilitate quenching of the product gases to prevent unselective by-product reactions. The primary separation enables removal of over 90 wt % of the dehydrogenation catalyst which reduces the mass of material that must be quench cooled and therefore reduces the volume of necessary quench material. Moreover, by not quenching over 90 wt % of the catalyst, heat is preserved in the catalyst which is necessary to drive the endothermic dehydrogenation reaction.

PDH catalyst is used in a dehydrogenation reaction process to catalyze the dehydrogenation of paraffins, such as ethane, propane, iso-butane, and n-butane, to olefins, such as ethylene, propylene, isobutene and n-butenes, respectively. The PDH process will be described exemplarily to illustrate the disclosed apparatus and process.

The conditions in the dehydrogenation reactor may include a temperature of about 500 to about 800° C., a pressure of about 40 to about 310 kPa and a catalyst to oil ratio of about 5 to about 100. The dehydrogenation reaction may be conducted in a fluidized manner such that gas, which may be the reactant paraffins with or without a fluidizing inert gas, is distributed to the reactor in a way that lifts the dehydrogenation catalyst in the reactor vessel while catalyzing the dehydrogenation of paraffins. During the catalytic dehydrogenation reaction, coke is deposited on the dehydrogenation catalyst leading to reduction of the activity of the catalyst. The dehydrogenation catalyst must then be regenerated.

An exemplary PDH reactor 12 is shown in the FIGURE. The PDH reactor 12 may comprise two chambers, a reaction chamber 14 and a separation chamber 26. A feed line 10 may deliver a reactant stream of feed to the reactor 12. The reactant stream may predominantly comprise propane or butane, but other paraffins such as ethane may be present in the reactant stream in conjunction with or to the exclusion of other paraffins. Any feed distributor can distribute the reactant stream to the reactor 12. A domed reactant distributor 32 may be utilized in the reaction chamber 14 of the reactor 12. The domed reactant distributor 32 receives a gaseous reactant stream and distributes the reactant stream through nozzles in the top dome of the domed reactant distributor 32 to distribute the reactant stream across the entire cross section of the reaction chamber 14. It is envisioned that other fluidizing gases may be used to also promote fluidization in the reaction chamber 14. In an embodiment, the distributed reactant stream ascends in the reaction chamber 14 and the reactor 12.

A recycle catalyst pipe 34 has an inlet 35 located in the separation chamber 26 and an outlet comprising a first catalyst inlet 39 which in an embodiment may be connected to a first catalyst distributor 36. The recycle catalyst pipe 34 delivers a first stream of recycled spent catalyst that has not undergone regeneration from the separation chamber 26 through the outlet and the first catalyst inlet 39 to the first section 38 of the reaction chamber 14 in an embodiment through the first catalyst distributor 36. The first catalyst inlet 39 and/or the first catalyst distributor 36 provides spent catalyst to a first section 38 of the reaction chamber 14. The recycled spent catalyst is fed to the reactor 12 through the first catalyst inlet 39 which is the outlet of the recycle catalyst pipe 34. The first catalyst inlet 39 and/or the first catalyst distributor 36 may be contained in the first reaction chamber 14.

The first catalyst distributor 36 can comprise a central pipe with pipes extending from the central pipe in varying angles to spread spent catalyst horizontally over the entire cross section of the reaction chamber 26. A gas assist which may comprise reactant gas or inert gas such a steam may be employed to compel the catalyst out the pipes of the first spent catalyst distributor 36. The gas assist may be delivered from a line through a nozzle 37 in an inlet to the first catalyst distributor 36. The recycled spent catalyst has been in contact with the reactant stream and not been subjected to regeneration. Thus, the recycled spent catalyst has a reduced average temperature resulting from the endothermicity of the reaction. However, the recycled spent catalyst still possesses sufficient enthalpy to catalyze and drive conversion of the reactant stream distributed by the reactant distributor 32. The average temperature of the first stream of catalyst may be about 500 to about 800° C. Consequently, the temperature of the first reaction section 38 may be about 450 to about 750° C.

In the first reaction section 38 the fresh reactant stream is contacted with the first stream of catalyst and the reactant paraffins begin undergoing conversion to olefins, typically propane to propylene. The endothermic dehydrogenation reaction withdraws heat from the mix of the first catalyst stream and the reactant stream while the catalyst and reactants are rising in the reactor impelled by the reactant stream continually entering the reactor through the reactant distributor 32.

To supply additional heat and catalyst to the reaction chamber 14, a second catalyst inlet 43 delivers a second catalyst stream to the reactor 12, in an embodiment through a second catalyst distributor 40. A regenerated catalyst pipe 16 has an inlet 17 located in a regenerator 20 and an outlet connected to the second catalyst inlet 43 and/or the second catalyst distributor 40. The regenerated catalyst pipe 16 delivers a second stream of regenerated catalyst from the regenerator 20 through the outlet to the second catalyst inlet 43 and/or the second catalyst distributor 40. The second catalyst inlet 43 and/or the second regenerated catalyst distributor 40 is contained in and provides hot regenerated catalyst to a second section 42 of the reaction chamber 14. The reactant stream is contacted with the second catalyst stream after contacting the reactant stream with the first catalyst stream. Moreover, the second catalyst stream has a higher temperature than the first catalyst stream.

The second regenerated catalyst distributor 40 may comprise a central pipe with pipes extending from the central pipe in varying angles to spread regenerated catalyst horizontally over the entire cross section of the reaction chamber 14. A gas assist which may comprise reactant gas or inert gas such a steam may be employed to compel the catalyst out the pipes of the second regenerated catalyst distributor 40. The gas assist may be delivered from a line through a nozzle 41 in an inlet to the second catalyst distributor 40. The regenerated catalyst has just undergone combustive regeneration and has a very hot average temperature and is active since coke deposits have been combusted from its surface. Hence in the second section 42 of the reaction chamber 14, the reactant stream is provided with additional enthalpy and catalyst to catalytically convert paraffins to olefins, typically propane to propylene. The average temperature of the second stream of catalyst may be about 500 to about 900° C. Consequently, the temperature of the second reaction section 42 may be about 400 to about 800° C. The first catalyst inlet 39 and/or the first catalyst distributor 36 is closer to the reactant distributor 32 than the second catalyst inlet 43 and/or the second catalyst distributor 40. The second catalyst inlet 39 may be spaced apart and may be above the first catalyst inlet 39. The second catalyst distributor 40 may be spaced apart and may be above the first catalyst distributor 36.

In the second reaction section 42 the reactant stream is contacted with the second stream of catalyst and the first stream of catalyst which mix together in the second reaction section, and the reactant paraffins undergo conversion to olefins, typically propane to propylene. The reactant stream and the first stream of catalyst and the second stream of catalyst rise in the reaction chamber 14 of the reactor 12 impelled by the reactant stream continually entering the reactor through the reactant distributor 32. At the interface 44, the fluid dynamics transition from a dense phase of catalyst below the transition to a fast-fluidized flow regime. The catalyst density in the dense phase of catalyst is at least 200 kg/m$^3$ (12.5 lb/ft$^3$); whereas the catalyst density in the fast-fluidized flow regime is at least 100 kg/m$^3$ (6.3 lb/ft). The superficial velocity of the reactant stream and the first stream of catalyst and the second stream of catalyst in the reaction chamber 14 will typically be at least about 0.9 m/s (3 ft/s), suitably at least about 1.1 m/s (3.5 ft/s), preferably at least 1.4 m/s (4.5 ft/s), to about 2.1 m/s (7 ft/s) to provide the fast-fluidized flow regime. Reactant gas and catalyst ascend in a fast-fluidized flow regime in which catalyst may slip relative to the gas and the gas can take indirect upward trajectories.

The dehydrogenation catalyst may be of any of a variety of catalysts suitable for a fluidized dehydrogenation unit. The dehydrogenation catalyst selected should minimize cracking reactions and favor dehydrogenation reactions. Suitable catalysts for use herein include amorphous material or molecular sieves which may be dispersed in a porous inorganic carrier material such as silica, aluminum, zirconium, or clay. An exemplary embodiment of a catalyst includes crystalline silica-alumina or silica-alumina-phosphate as the primary active component, a matrix, a binder, and a filler.

The matrix component may include amorphous alumina or silica, and the binder and filler provide physical strength and integrity. Silica sol or alumina sol may be used as the binder and kaolin clay may be used as the filler. The catalyst particles may have a nominal diameter of about 20 to about 150 micrometers with the average diameter of about 70 to about 90 micrometers.

The dehydrogenation catalyst may support a dehydrogenation metal. The dehydrogenation metal may be a one or a combination of transition metals. A noble metal may be a preferred dehydrogenation metal; however, a IIB or a IIIB metal may be a suitable dehydrogenation metal alone or in combination with other dehydrogenation metals. Iron, tungsten, gallium, copper, zinc or zirconium alone or in combination with each other or a noble metal may be suitable dehydrogenation metals. Combustion promoters may be utilized in addition to the catalyst. Metals may be incorporated into the lattice structure of the molecular sieve.

The acid function of the catalyst should be minimized to prevent cracking and favor dehydrogenation. Alkali metals and alkaline earth metals may be also be included in the catalyst to attenuate the acidity of the catalyst. Rare earth metals may be included in the catalyst to control the activity of the catalyst. Concentrations of 0.05 to 10 wt % metals may be incorporated into the catalyst. In the case of the noble metals, such as platinum, it is preferred to use about 0.05 to about 2 wt % noble metal.

The reactant stream lifts the first stream of catalyst mixed with the second stream of catalyst upwardly in the reaction chamber while paraffins convert to olefins in the presence of the dehydrogenation catalyst which gradually becomes spent catalyst attributed to the agglomeration of coke deposits on the catalyst. A fluidizing inert gas may be distributed to the reaction chamber to assist in lifting the mixture of catalyst and reactants upwardly in the reaction chamber 14. The reactant gases convert to product gases while ascending in the reaction chamber 14. The blend of gases and catalyst ascend from the reaction chamber 14 through a frustoconical transition section 45 into a transport riser 46 which has a smaller diameter than the diameter 40 of the combustion chamber 20. The separation chamber 26 is in downstream communication with the reaction chamber 14 through the riser 46. A blend of gases and catalyst accelerate in the narrower transport riser 46 and are discharged from a primary catalyst separator 48 into the separation chamber 26. The primary catalyst separator 48 may be a riser termination device that utilizes horizontal, centripetal acceleration to separate spent catalyst from product gas. Arcuate ducts of the primary catalyst separator 48 direct the mixture of olefinic product gas and spent catalyst to exit from the riser 46 in a typically horizontally angular direction to centripetally accelerate causing the denser catalyst to gravitate outwardly. The catalyst loses angular momentum and falls into a lower catalyst bed 49 depicted with an upper interphase. The lighter gases ascend in the separation chamber 26 and enter into cyclones 50, 52. The cyclones 50, 52 may comprise first and second cyclonic stages of separation to further remove catalyst from product gases. The olefinic product gas is ducted to a plenum 54 from which it is discharged from the reactor 12 through a product outlet 56 in a product line. The first catalyst inlet 39 and the second catalyst inlet 43 are closer to the reactant distributor 32 than to the product outlet 56. The primary catalyst separator 48 is located closer to the first catalyst inlet 39 and the second catalyst inlet 43 than the product outlet 56. In an embodiment, the first catalyst distributor 36 and the second catalyst distributor 40 are closer to the reactant distributor 32 than to the product outlet 56. Additionally, the primary catalyst separator 48 is located closer to the first catalyst distributor 36 and the second catalyst distributor 40 than the product outlet 56. The superficial gas velocity in the transport riser 46 will be about 12 m/s (40 ft/s) to about 20 m/s (70 ft/s) and have a density of about 64 kg/m$^3$ (4 lb/ft$^3$) to about 160 kg/m$^3$ (10 lb/ft$^3$), constituting a dilute catalyst phase.

Catalyst separated from the product gas by the primary catalyst separator 48 drops into a dense catalyst bed 49. In an aspect, primary cyclones 50 may collect product gas from the separation chamber 26 and transport the product gas separated from catalyst to a secondary cyclone 52 to further separate catalyst from the product gas before directing secondarily purified product gas to the plenum 54. Catalyst separated from product gas in the cyclones 50, 52 is dispensed by dip legs into the dense catalyst bed 49. At this point, the separated catalyst in the separation chamber 26 is considered spent catalyst because deposits of coke are agglomerated thereon. A regeneration portion of the spent catalyst collected in the dense bed 49 in the separation chamber 26 is transported in a spent catalyst pipe 18 to a catalyst regenerator 20 to have coke burned from the catalyst to regenerate and heat the dehydrogenation catalyst. A vertical section of the spent catalyst pipe 18 may comprise a stripping section 60. A stripping gas such a steam or another inert gas may be fed into a lower end of the stripping section 60 to strip hydrocarbons from the spent catalyst entering the stripping section 60. Baffles may also be provided in the stripping section 60 to cause the spent catalyst to wend laterally in the stripping section to expose more catalyst particles to upwardly flowing stripping gas.

A recycle portion of the spent catalyst collected in the dense bed 49 of the separation chamber 26 enters the recycle catalyst pipe 34 through the inlet 35. The recycle portion of the spent catalyst is recycled in the recycle catalyst pipe 34 back to the first catalyst inlet 39 and/or the first catalyst distributor 36 in the reaction chamber 14 of the reactor 12 as the first catalyst stream. The recycle portion of the spent catalyst is not regenerated before it returns to the reaction chamber 14.

The separation chamber 26 may include a disengagement can 70 that surrounds the upper end of the riser 46 and the primary separator 48. A vertical wall 71 of the disengagement can 70 is spaced apart from a shell 27 of the separation chamber 26 of the reactor 12 to define an annulus 72 therebetween. Dip legs of the cyclones 50 and 52 may be located in the annulus 72. The disengagement can 70 contains and confines the olefinic product gas in a contained space 75 that may be defined by the vertical wall 71. The contained space has a volume that is smaller than the volume of the reactor 12, and specifically, smaller than the reaction chamber 26, at the same elevation. In an embodiment, the contained space 75 has a cross section that is smaller than the cross section of the reactor 12 at the same elevation. The contained space 75 defined by the disengagement can 70 serves to limit travel of the product gas exiting the primary separator 48 at reactor temperature, so as to reduce its time in the reactor 12, thereby mitigating unselective cracking reactions to undesired products.

The top of the disengagement can 70 may be hemispherical and feed a gas recovery conduit 74 extending from a center of the top. The gas recovery conduit 74 is contiguous with the disengagement can 70 and further defines the contained space 75. The gas recovery conduit 74 transports olefinic product gases to ducts 76 that are directly ducted or connected to the primary cyclones 50. The direct ducting from the disengagement can 70 to the primary cyclones 50 also prevents product gas from getting loose in the larger volume of the reactor 12 where excessive residence time may occur to permit unselective cracking. Dehydrogenation catalyst separated from the olefinic product gas by the primary catalyst separator 48 drops into a dense catalyst bed 49 within the contained space 75.

Diplegs 51, 53 of the cyclones 50, 52, respectively, dispense spent dehydrogenation catalyst to the dense dehydrogenation catalyst bed 49 in the annulus 72. Windows 82 in the lower section of the wall 71 of the disengagement can 70 permit catalyst confined in the disengagement can to move into the annulus 72 and enter into the recycle catalyst pipe 34 or the regeneration pipe 18. A baffle 84 which may be annular is disposed in the annulus 71 above the dense catalyst bed 49 and above the windows 82 to prevent product vapors from rising in the annulus 72 into the large free volume section of the reactor 12 which would increase hot residence time of the product vapors in the reactor and allow reaction to unselective by-products. Apertures 85 in the baffle 84 permit dip legs 51, 53 to extend through the baffle for dispensing catalyst into the dense catalyst bed 49 below the baffle in the annulus 72. Distributors 86 may distribute dome steam above the baffle 84 to ensure that no olefinic product vapors from the dense bed 49 travel from below the baffle through the apertures 85 into the large open volume in the reactor 12. Due to the higher pressure of the dome steam, all gas travel will be one-way down through apertures 85 instead of upwardly in the reverse.

A quench fluid such as condensed product liquid or even cool catalyst may be injected into the product gases through a quench nozzle 80 to cool the product gases to below cracking temperature to limit unselective cracking. Quench fluid is advantageously injected into the contained space 75. The quench fluid may be injected into the contained space 75 defined by the gas recovery conduit 74 which directs and confines the separated olefinic product gas to a narrowed location to facilitate quenching. The quench nozzle 80 may be in upstream communication with the gas recovery conduit 74 in the contained space 75. The gas recovery conduit 74 is in downstream communication with the primary catalyst separator 48 which separates the predominance of the spent catalyst from the product gases. The spent catalyst bypasses quenching to retain heat in the catalyst. The product gases separated from the predominance of the catalyst subjects a reduced mass of material to quenching thereby requiring less volume of quench fluid to achieve sufficient cooling to reduce the temperature of product gas to below cracking temperature. The operation of the disengagement can 70 enables containment and capture of olefinic product gases and a vastly reduced mass of catalyst. The gas recovery conduit 74 directs the olefinic product gas to a narrowed location to effectively expose it to a quench material injected into the gas recovery conduit. The quench material may be water or hydrocarbon, such as paraffins recovered from a downstream dehydrogenation product recovery process.

The stripped, spent dehydrogenation catalyst is transported by the spent catalyst pipe 18 to the regenerator 20 to combust the coke on the spent catalyst and regenerate the spent catalyst into regenerated catalyst. The catalyst regenerator 20 includes a combustion chamber 21 and a catalyst separator 23 which separates regenerated catalyst from flue gas generated in the combustion chamber 21 as they are discharged from the catalyst separator 23. An oxygen supply gas is provided to the combustion chamber 21 which lifts the spent catalyst in the combustion chamber 21 through the catalyst separator 23 and into a separation chamber 25. The coke is burned off the spent catalyst by contact with the oxygen supply gas at regeneration conditions. In an exemplary embodiment, air is used as the oxygen supply gas, because air is readily available and provides sufficient oxygen for combustion. About 10 to about 15 kg of air are required per kg of coke burned off of the spent catalyst. Exemplary regeneration conditions include a temperature from about 500° C. (900° F.) to about 900° C. (1700° F.) and a pressure of about 103 kPa (abs) (15 psia) to about 450 kPa (abs) (70 psia) in the regenerator 20. Hydrocarbon fuel may be added to the regenerator 20 such as through nozzles 28 to boost the heat generated in the regenerator to drive the reaction in the reactor 12.

Regenerated catalyst is returned to the reactor 12 in the regenerated catalyst pipe 16. The regenerated catalyst pipe 16 has an inlet 17 connected to the regenerator 20 in the separation chamber 25 through which regenerated catalyst from the regenerator is transported to the second catalyst distributor 40 in the reactor 12 as the hotter second stream of catalyst. The regenerated catalyst is fed to the reactor 12 through the second catalyst inlet 43 which is the outlet of the regenerated catalyst pipe 16. The regenerated catalyst pipe 16 is connected to the second catalyst inlet 43 which can deliver the regenerated catalyst to the reactor 12 without means of a distributor.

The embodiments herein provide a process and apparatus for dehydrogenating a paraffinic stream with confined quenching to produce product with higher selectivity to propylene.

EXAMPLE

We simulated a dehydrogenation process in a 1000 kilometric ton per year unit using the process and apparatus described herein. We conducted two simulations both at 43% conversion but one with quench and one without quench. The selectivity to propylene was 87.7 wt % with quench; whereas, selectivity to propylene was only 78.4 wt % without quench. Selectivity was improved by almost 9 wt % by use of quench.

SPECIFIC EMBODIMENTS

While the following is described in conjunction with specific embodiments, it will be understood that this description is intended to illustrate and not limit the scope of the preceding description and the appended claims.

A first embodiment of the invention is a process for contacting a paraffin stream with dehydrogenation catalyst comprising distributing a paraffin stream to a reactor; contacting the reactant stream with a dehydrogenation catalyst stream to produce olefinic product gases and spent dehydrogenation catalyst; separating a spent dehydrogenation catalyst stream from an olefinic product gas stream in a primary separator; containing the olefinic product gas in a contained space having a volume smaller than the volume of the reactor at the same elevation; quenching the olefinic product gases in the contained space; and discharging the olefinic product gases from the reactor. An embodiment of the invention is one, any or all of prior embodiments in this paragraph up through the first embodiment in this paragraph wherein the contained space has a wall that is spaced apart from a shell of the reactor. An embodiment of the invention is one, any or all of prior embodiments in this paragraph up through the first embodiment in this paragraph further comprising a plurality of cyclone separators in the separation chamber and ducting the olefinic product gases from the contained space into the cyclone separators. An embodiment of the invention is one, any or all of prior embodiments in this paragraph up through the first embodiment in this paragraph further comprising separating a spent dehydrogenation catalyst from the olefinic product gases in the cyclone separators and dispensing the dehydrogenation catalyst by dip legs of the cyclone separators through a baffle into a dense dehydrogenation catalyst bed. An embodiment of the invention is one, any or all of prior embodiments in this paragraph up through the first embodiment in this paragraph wherein the spent dehydrogenation catalyst stream separated from the olefinic product gases in the primary separator falls into the dense dehydrogenation catalyst bed. An embodiment of the invention is one, any or all of prior embodiments in this paragraph up through the first embodiment in this paragraph wherein the spent dehydrogenation catalyst stream separated from the olefinic product gases in the primary separator fall in the dense dehydrogenation catalyst bed in the contained space and further comprising windows in the wall of the contained space and the spent dehydrogenation catalyst in the dense dehydrogenation catalyst bed moving from the contained space into an annulus between the wall and a shell of the reactor. An embodiment of the invention is one, any or all of prior embodiments in this paragraph up through the first embodiment in this paragraph further comprising regenerating a portion of the spent dehydrogenation catalyst from the annulus to provide a regenerated dehydrogenation catalyst stream and returning the regenerated dehydrogenation catalyst stream to the contacting step. An embodiment of the invention is one, any or all of prior embodiments in this paragraph up through the first embodiment in this paragraph further comprising recycling another portion of the spent dehydrogenation catalyst from the spent dehydrogenation catalyst in the annulus without regeneration to the contacting step. An embodiment of the invention is one, any or all of prior embodiments in this paragraph up through the first embodiment in this paragraph further comprising compelling the paraffin reactant stream and the dehydrogenation catalyst stream to flow upwardly from a reaction chamber through a riser into a separation chamber comprising the primary separator and the contained space.

A second embodiment of the invention is a process for contacting a paraffin stream with dehydrogenation catalyst comprising distributing a paraffin stream to a reaction chamber of a reactor; contacting the reactant stream with a dehydrogenation catalyst stream to produce olefinic product gases and spent dehydrogenation catalyst; separating a spent dehydrogenation catalyst stream from an olefinic product gas stream in a primary separator surrounded by a disengagement can; directing the olefinic product gases separated from the spent dehydrogenation catalyst stream through a gas recovery conduit; quenching the olefinic product gases in the gas recovery conduit; and discharging the olefinic product gases from the reactor. An embodiment of the invention is one, any or all of prior embodiments in this paragraph up through the second embodiment in this paragraph further comprising injecting quench material into the gas recovery conduit. An embodiment of the invention is one, any or all of prior embodiments in this paragraph up through the second embodiment in this paragraph wherein the disengagement can is spaced apart from a shell of the reactor. An embodiment of the invention is one, any or all of prior embodiments in this paragraph up through the second embodiment in this paragraph further comprising a plurality of cyclone separators in the separation chamber and ducting the olefinic product gases from the gas recovery conduit to the cyclone separators. An embodiment of the invention is one, any or all of prior embodiments in this paragraph up through the second embodiment in this paragraph further comprising separating a spent dehydrogenation catalyst from the olefinic product gases in the cyclone separators and dispensing the dehydrogenation catalyst by dip legs of the cyclone separators through a baffle into a dense catalyst bed. An embodiment of the invention is one, any or all of prior embodiments in this paragraph up through the second embodiment in this paragraph further wherein the spent dehydrogenation catalyst stream separated from the olefinic product gases in the primary separator falls into a dehydrogenation catalyst bed and further comprising regenerating a portion of the spent catalyst to provide a regenerated first dehydrogenation catalyst stream and returning the first dehydrogenation catalyst stream to the reaction chamber. A dehydrogenation reactor for contacting a paraffinic reactant stream with a dehydrogenation catalyst comprising a reaction chamber containing a catalyst inlet for feeding dehydrogenation catalyst to the reactor and a reactant distributor for distributing the paraffinic reactant stream to the dehydrogenation reactor; a separation chamber in communication with the reaction chamber, the separation chamber comprising a primary catalyst separator for separating catalyst from product gases and a gas recovery conduit; a disengagement can surrounding the primary catalyst separator; a gas recovery conduit extending from the disengagement can; a quench nozzle in communication with the gas recovery conduit for injecting a quench material into the gas recovery conduit; a product outlet for discharging product from the reactor. The reactor of claim 10 wherein a wall of the disengagement can is spaced apart from a shell of the separation chamber to define an annulus. The reactor of claim 10 further comprising a plurality of cyclone separators in the separation chamber and a direct duct from the gas recovery conduit to the cyclone separators. The reactor of claim 12 further comprising a baffle extending across the annulus and a dip leg of a cyclone protruding through an aperture in the baffle. The reactor of claim 13 further comprising windows in the wall of the disengagement can to allow catalyst to pass between the disengagement can and the annulus.

A third embodiment of the invention is a process for contacting a paraffin reactant stream with dehydrogenation catalyst comprising feeding the paraffin reactant stream to a reactor; contacting the paraffin reactant stream with a first dehydrogenation catalyst stream to produce olefin product gases; contacting the paraffin reactant stream with a second dehydrogenation catalyst stream to produce olefin product gases after contacting the reactant paraffin stream with the first dehydrogenation catalyst stream, the second dehydrogenation catalyst stream having a higher temperature than the first dehydrogenation catalyst stream; separating the first dehydrogenation catalyst stream and the second dehydrogenation catalyst stream from the olefin product gases; and discharging the olefin product gases from the reactor. An embodiment of the invention is one, any or all of prior embodiments in this paragraph up through the third embodiment in this paragraph wherein the first dehydrogenation catalyst stream and the second dehydrogenation catalyst separated from the olefin product gases comprise spent dehydrogenation catalyst and further comprising regenerating a portion of the spent dehydrogenation catalyst to provide the second dehydrogenation catalyst stream and recycling another portion of the spent dehydrogenation catalyst to provide the first dehydrogenation catalyst stream. An embodiment of the invention is one, any or all of prior embodiments in this paragraph up through the third embodiment in this paragraph further comprising contacting the paraffin reactant stream with the first dehydrogenation catalyst stream and the second dehydrogenation catalyst stream in a first chamber and separating the first dehydrogenation catalyst stream and the second dehydrogenation catalyst stream from the olefin product gases in a second chamber to provide spent dehydrogenation catalyst. An embodiment of the invention is one, any or all of prior embodiments in this paragraph up through the third embodiment in this paragraph further comprising compelling the paraffin reactant stream and the first dehydrogenation catalyst stream and the second dehydrogenation catalyst stream to flow upwardly in the reactor.

Without further elaboration, it is believed that using the preceding description that one skilled in the art can utilize the present disclosure to its fullest extent and easily ascertain the essential characteristics of this disclosure, without departing from the spirit and scope thereof, to make various changes and modifications of the disclosure and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for contacting a paraffin stream with dehydrogenation catalyst comprising:
   distributing a paraffin stream to a reactor;
   contacting said reactant stream with a dehydrogenation catalyst stream to produce olefinic product gases and spent dehydrogenation catalyst;
   separating a spent dehydrogenation catalyst stream from an olefinic product gas stream in a primary separator;
   containing said olefinic product gas in a contained space having a volume smaller than the volume of the reactor at the same elevation;
   quenching said olefinic product gases in said contained space; and
   discharging said olefinic product gases from said reactor.

2. The process of claim 1 wherein said contained space has a wall that is spaced apart from a shell of the reactor.

3. The process of claim 2 further comprising a plurality of cyclone separators in said separation chamber and ducting said olefinic product gases from said contained space into said cyclone separators.

4. The process of claim 3 further comprising separating a spent dehydrogenation catalyst from said olefinic product gases in said cyclone separators and dispensing said dehydrogenation catalyst by dip legs of said cyclone separators through a baffle into a dense dehydrogenation catalyst bed.

5. The process of claim 4 wherein said spent dehydrogenation catalyst stream separated from said olefinic product gases in said primary separator falls into said dense dehydrogenation catalyst bed.

6. The process of claim 5 wherein said spent dehydrogenation catalyst stream separated from said olefinic product gases in said primary separator fall in said dense dehydrogenation catalyst bed in said contained space and further comprising windows in said wall of said contained space and said spent dehydrogenation catalyst in said dense dehydrogenation catalyst bed moving from said contained space into an annulus between said wall and a shell of said reactor.

7. The process of claim 6 further comprising regenerating a portion of said spent dehydrogenation catalyst from said annulus to provide a regenerated dehydrogenation catalyst stream and returning said regenerated dehydrogenation catalyst stream to said contacting step.

8. The process of claim 7 further comprising recycling another portion of said spent dehydrogenation catalyst from said spent dehydrogenation catalyst in said annulus without regeneration to said contacting step.

9. The process of claim 1 further comprising compelling the paraffin reactant stream and the dehydrogenation catalyst stream to flow upwardly from a reaction chamber through a riser into a separation chamber comprising said primary separator and said contained space.

10. A process for contacting a paraffin stream with dehydrogenation catalyst comprising:
    distributing a paraffin stream to a reaction chamber of a reactor;
    contacting said reactant stream with a dehydrogenation catalyst stream to produce olefinic product gases and spent dehydrogenation catalyst;
    separating a spent dehydrogenation catalyst stream from an olefinic product gas stream in a primary separator surrounded by a disengagement can;
    directing said olefinic product gases separated from said spent dehydrogenation catalyst stream through a gas recovery conduit;
    quenching said olefinic product gases in said gas recovery conduit; and
    discharging said olefinic product gases from said reactor.

11. The process of claim 10 further comprising injecting quench material into said gas recovery conduit.

12. The process of claim 10 wherein said disengagement can is spaced apart from a shell of the reactor.

13. The process of claim 10 further comprising a plurality of cyclone separators in said separation chamber and ducting said olefinic product gases from said gas recovery conduit to said cyclone separators.

14. The process of claim 13 further comprising separating a spent dehydrogenation catalyst from said olefinic product gases in said cyclone separators and dispensing said dehydrogenation catalyst by dip legs of said cyclone separators through a baffle into a dense catalyst bed.

15. The process of claim 14 further wherein said spent dehydrogenation catalyst stream separated from said olefinic product gases in said primary separator falls into a dehydrogenation catalyst bed and further comprising regenerating a portion of said spent catalyst to provide a regenerated first dehydrogenation catalyst stream and returning the first dehydrogenation catalyst stream to said reaction chamber.

16. A dehydrogenation reactor for contacting a paraffinic reactant stream with a dehydrogenation catalyst comprising:
    a reaction chamber containing a catalyst inlet for feeding dehydrogenation catalyst to the reactor and a reactant distributor for distributing the paraffinic reactant stream to the dehydrogenation reactor;
    a separation chamber in communication with the reaction chamber, said separation chamber comprising a primary catalyst separator for separating catalyst from product gases and a gas recovery conduit;
    a disengagement can surrounding said primary catalyst separator;
    a gas recovery conduit extending from said disengagement can;
    a quench nozzle in communication with said gas recovery conduit for injecting a quench material into said gas recovery conduit;
    a product outlet for discharging product from the reactor.

17. The reactor of claim 10 wherein a wall of said disengagement can is spaced apart from a shell of said separation chamber to define an annulus.

18. The reactor of claim 10 further comprising a plurality of cyclone separators in said separation chamber and a direct duct from said gas recovery conduit to said cyclone separators.

19. The reactor of claim 12 further comprising a baffle extending across said annulus and a dip leg of a cyclone protruding through an aperture in said baffle.

20. The reactor of claim 13 further comprising windows in said wall of said disengagement can to allow catalyst to pass between said disengagement can and said annulus.

\* \* \* \* \*